(12) United States Patent
Placik

(10) Patent No.: US 8,372,047 B1
(45) Date of Patent: Feb. 12, 2013

(54) DEVICE AND METHOD FOR TOPICALLY APPLYING MEDICATION TO THE LIPS

(76) Inventor: Otto J. Placik, Arlington Heights, IL (US)

( * ) Notice: Subject to any disclaimer, the term of this patent is extended or adjusted under 35 U.S.C. 154(b) by 112 days.

(21) Appl. No.: 13/019,473

(22) Filed: Feb. 2, 2011

(51) Int. Cl.
*A61M 35/00* (2006.01)
*A61M 31/00* (2006.01)
*A61J 7/00* (2006.01)

(52) U.S. Cl. ............ 604/290; 604/19; 604/27; 604/28; 604/48; 604/77; 604/93.01; 604/112; 604/113; 604/181; 604/285; 604/291; 604/309; 604/310; 604/500; 604/512; 604/514; 604/518

(58) Field of Classification Search .................. None
See application file for complete search history.

(56) References Cited

U.S. PATENT DOCUMENTS

| | | | | |
|---|---|---|---|---|
| 1,735,221 A | * | 11/1929 | Temple | 604/77 |
| 4,338,928 A | * | 7/1982 | Martin et al. | 128/857 |
| 2003/0209254 A1 | * | 11/2003 | Ruggiero | 132/320 |
| 2009/0035718 A1 | * | 2/2009 | Coffee | 433/93 |

* cited by examiner

*Primary Examiner* — Melanie Hand
*Assistant Examiner* — Joshua Lee
(74) *Attorney, Agent, or Firm* — LaMorte & Associates P.C.

(57) ABSTRACT

A system and method of topically applying an anesthetic, or other medication, to one or both lips of the mouth. An applicator device is provided that has a curved first wall, a curved second wall, and a horizontal shelf that joins the first wall to the second wall. The first wall, the second wall and the horizontal shelf combine to define either one or two curved lip compartments. A volume of the anesthetic, or other medication, is placed within the curved lip compartments. The applicator device is partially placed in a person's mouth so that the second wall is positioned between the back of the lips and in front of the teeth. While in this position, the lip of the user passes into the curved lip compartment and is contacted by the anesthetic.

16 Claims, 5 Drawing Sheets

DEVICE AND METHOD FOR TOPICALLY APPLYING MEDICATION TO THE LIPS

BACKGROUND OF THE INVENTION

1. Field of the Invention

In general, the present invention relates to devices that create a barrier around the lips of the mouth. More particularly, the present invention relates to devices that are capable of retaining a volume of material and retaining that material in constant contact with the lips for a prolonged period of time.

2. Prior Art Description

The lips of a person's mouth contain a particularly high density of nerve endings. This makes the lips very sensitive to the sense of touch. Furthermore, the dermis layer on the lips is thin as compared to other areas of the face. This adds to the sensitivity of the lips. It also makes the lips more prone to bleeding as compared to other areas of the face. To further complicate matters, the lips contain a high density of blood vessels. This cause the lips to bleed easily when injured. It also causes the lips to easily swell when injured. This anatomy is the underlying cause of the ease of receiving a "fat lip" even when the lips have received only a small injury.

Because the lips are highly sensitive, physicians often want to numb the lips before any medical procedure is performed on the lips. The numbing of the lips is traditionally preformed in one of two ways.

For minor procedures, topical anesthetics can be applied to the exterior of the lip. The topical anesthetic numbs the exterior of the lip. The topical anesthetic is typically applied by a physician rubbing the anesthetic onto the exterior of the lip with a swab or similar implement. As a result, only a small amount of anesthetic is applied. Therefore, the numbing effect is very localized and typically does not numb nerve endings located deep within the lip tissue or on the interior of the lip. Consequently, if the lips are to receive injections, stitches, piercings, or any other treatment that affects the deeper tissue of the lip, the patient can still experience a significant amount of discomfort.

The second method of numbing lips is to numb the lips with injections of anesthetics. This completely numbs the tissue of the lip. However, the act of injecting the anesthetic causes discomfort and injury to the lip. Furthermore, injecting the anesthetic may cause some swelling of the lips. If a physician is performing a cosmetic procedure on the lips, such as fattening the lips with collagen, any swelling can cause obvious difficulties in the procedure as the doctor attempts to balance the shape of the lips.

A need therefore exists for an improved device and method for numbing the lips that does not injure the lips or otherwise cause swelling of the lips. A need also exists for a new device and method for numbing the lips that can use topical anesthetics in amounts great enough to numb the exterior of the lip, the interior of the lip, and all the tissue there between. These needs are met by the present invention as described and claimed below.

SUMMARY OF THE INVENTION

The present invention is a system and method of topically applying an anesthetic, or other medication, to the upper lip and/or the lower lip of a user. An applicator device is provided that has a curved first wall, a curved second wall, and a horizontal shelf that joins the first wall to the second wall. The first wall, the second wall and the horizontal shelf combine to define both an upper lip compartment and a lower lip compartment.

A volume of the anesthetic, or other medication, is placed within either the upper lip compartment or the lower lip compartment. The applicator device is partially placed in a person's mouth so that the second wall is positioned between the back of the lips and in front of the teeth. While in this position, the upper lip passes into the upper lip compartment and the lower lip passes into the lower lip compartment. Within the upper and lower compartments, the upper lip and the lower lip are contacted by the anesthetic. This enables the anesthetic to completely numb all the tissue of the lips. Once the lip tissue is completely numb, the applicator device is removed and the lips stand ready for a medical procedure.

BRIEF DESCRIPTION OF THE DRAWINGS

For a better understanding of the present invention, reference is made to the following description of exemplary embodiments thereof, considered in conjunction with the accompanying drawings, in which.

DETAILED DESCRIPTION OF THE DRAWINGS

Figure 1:
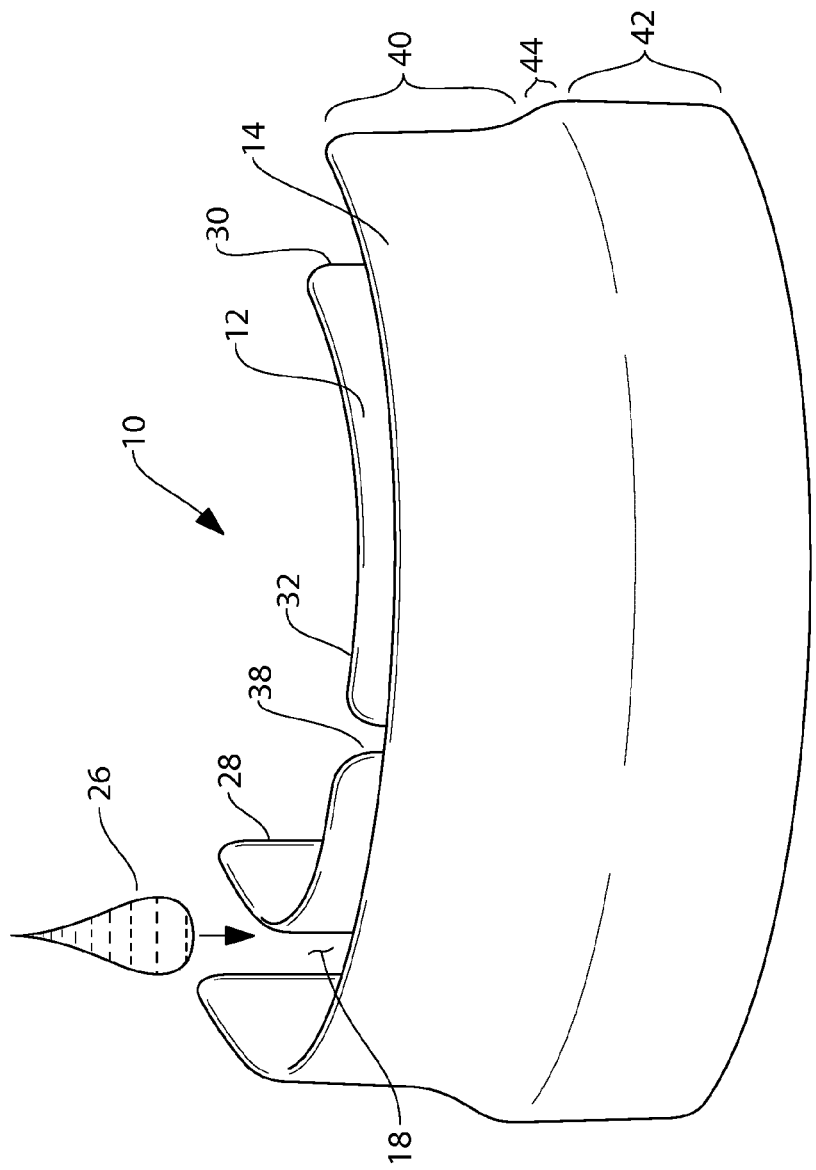
FIG. 1 is a front perspective view of an exemplary embodiment of an applicator device.
Figure 2:
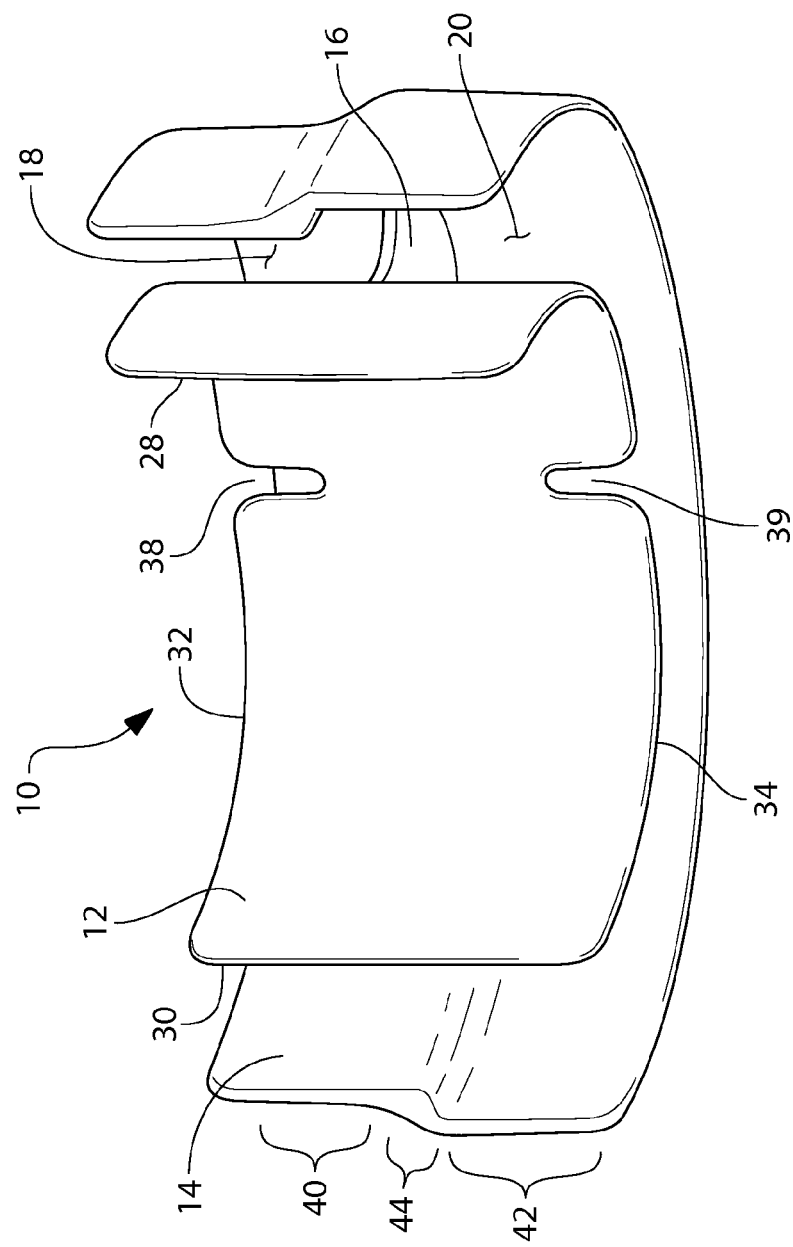
FIG. 2 is a rear perspective view of the exemplary embodiment of FIG. 1.
Figure 3:
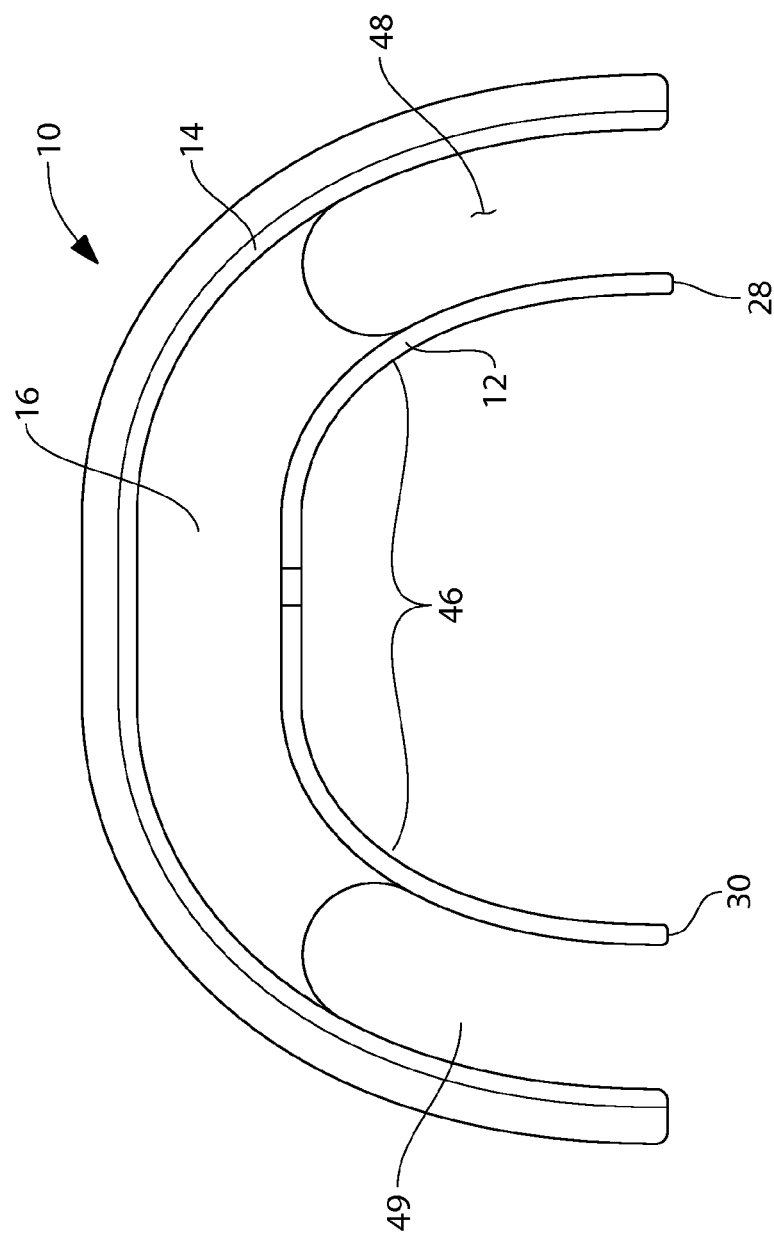
FIG. 3 is a top view of the exemplary embodiment of FIG. 1.
Figure 4:
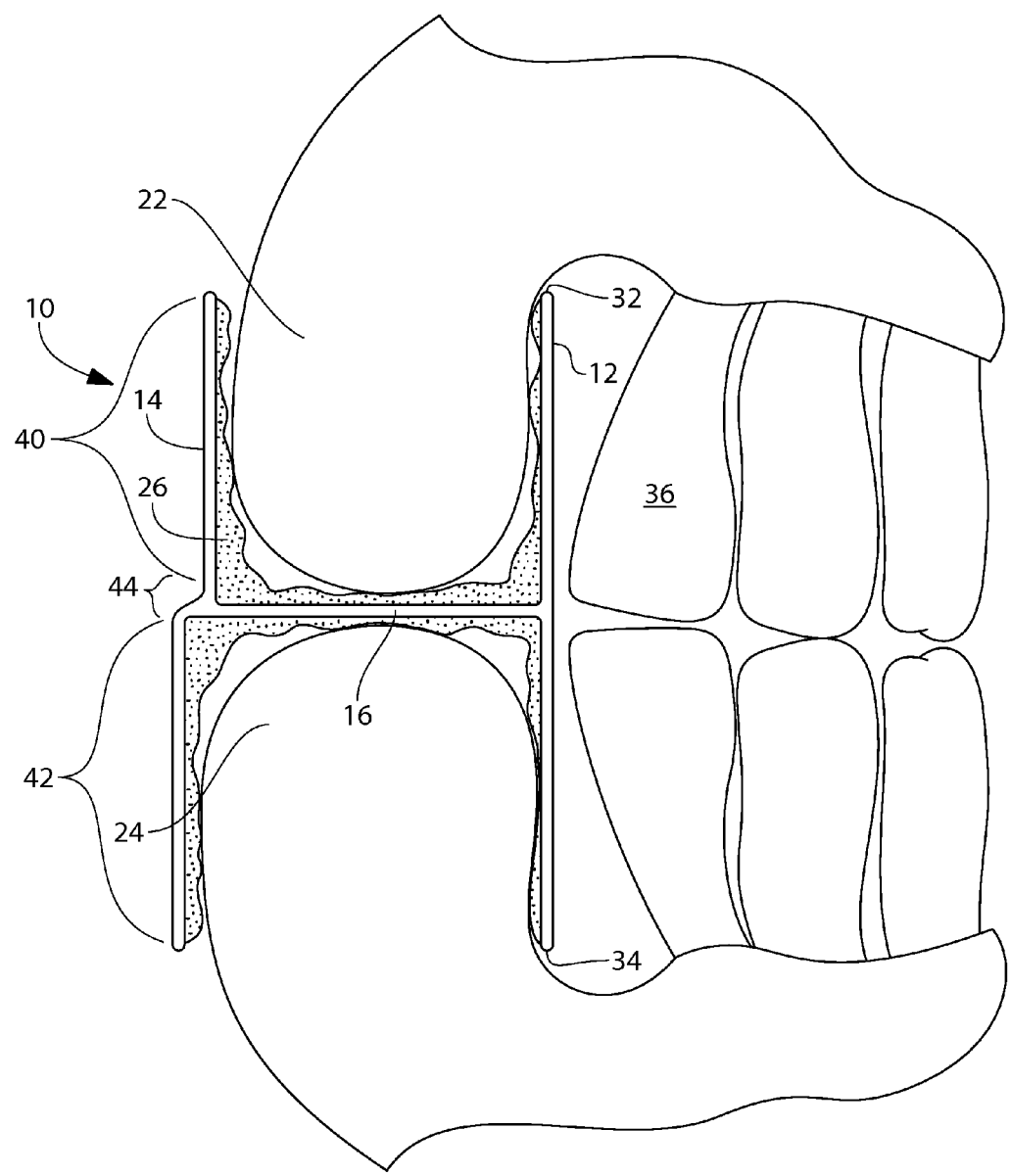
FIG. 4 is a cross-sectional view of the exemplary embodiment shown positioned in a user's mouth.

Although the present invention device and method can be used to apply medication to only the upper lip or the lower lip, the embodiment illustrated shows the device configured to apply medication to both the upper lip and the lower lip. This embodiment is selected in order to set forth the best mode contemplated for the invention. The illustrated embodiment, however, is merely exemplary and should not be considered a limitation when interpreting the scope of the appended claims.

Referring in combination to FIG. 1, FIG. 2, FIG. 3, and FIG. 4, the exemplary embodiment of the present invention applicator device 10 is illustrated. The applicator device 10 has an inner vertical wall 12 and an outer vertical wall 14 that are joined together by a horizontal shelf 16. The inner vertical wall 12, the outer vertical wall 14 and the horizontal shelf 16 combine to create a curved upper lip chamber 18 and a curved lower lip chamber 20. As will be explained in more detail, the upper lip chamber 18 is sized to receive the upper lip 22 of a patient. The lower lip chamber 20 is larger and is sized to receive the lower lip 24 of a patient. Both the upper lip chamber 18 and the lower lip chamber 20 are filled with a viscous topical medication 26, such as a topical anesthetic. The patient's lips 22, 24 are placed into the applicator device 10, wherein the patient's lips 22, 24 come into contact with the medication 26. The lips 22, 24 remain in contact with the medication 26 for as long as the lips 22, 24 are in the applicator device 10. In this manner, the patient's lips 22, 24 are kept in contact with a substantial amount of medication 26 for a prolonged period of time. If the medication 26 is a topical anesthetic, the anesthetic numbs both the inside and the outside of the lips 22, 24. Furthermore, the anesthetic can be applied to the lips in a volume sufficient, and for a time sufficient, to numb nerve endings deep within the lips 22, 24.

The inner vertical wall 12 has a first end 28, a second end 30, a top edge 32, and a bottom edge 34. The inner vertical wall 12 is curved. The curvature of the inner vertical wall 12 should be sufficient enough to pass around the exterior of the user's teeth 36. For an adult, the closest distance D1 between the opposite ends 28, 30 of the inner vertical wall 12 is between 2 inches and three inches, with approximately 2.5 inches being preferred. Smaller sizes can be used for small adults, adolescents, and children.

The inner vertical wall 12 preferably has a thickness of between 0.05 inches and 0.15 inches so as to be thin enough to comfortably fit between a patients lips 22, 24 and teeth 36. The height of the inner vertical wall 12, from its bottom edge 34 to its top edge 32, is between one inch and two inches, with approximately 1.5 inches being preferred. This height enables the inner vertical wall 12 to securely fit in the user's mouth behind the lips 22, 24 and in front of the teeth 36. However, the height of the inner vertical wall 12 is too tall to enable the mouth to close if the inner vertical wall 12 were accidentally positioned behind the teeth 36. The applicator device 10 is therefore very structurally different from a traditional sports mouthpiece that surrounds the teeth rather than the lips.

Two small reliefs 38, 39 are formed into the inner vertical wall 12 at its midpoint. An upper relief 38 is formed into the top edge 32 of the inner vertical wall 12. Likewise, a lower relief 39 is formed into the bottom edge 34 of the inner vertical wall 12. The upper relief 38 and the lower relief 39 are provided so that the inner vertical wall 12 does not interfere with the superior labial frenulum and the inferior labial fermium that extend between the lips 22, 24 and gums, respectively.

The outer vertical wall 14 has an upper section 40 and a lower section 42 that join in a transition zone 44. The upper section 40 follows the curvature of the inner vertical wall 12 and maintains a constant distance of approximately 0.50 inches from the inner vertical wall 12. This gap space is sufficient to accommodate the upper lip 22 of most adults.

The lower section 42 follows the curvature of the inner vertical wall 12 and maintains a constant distance of approximately 0.625 inches from the inner vertical wall 12. This large gap space is sufficient to accommodate the lower lip 24 of most adults.

The horizontal ledge 16 joins the inner vertical wall 12 to the outer vertical wall 14. The horizontal ledge 16 joins the inner vertical wall 12 to the outer vertical wall 14 in a connection zone 46 that is centered about the midpoint of both the inner vertical wall 12 and the outer vertical wall 14. This leaves open areas 48, 49 between the inner vertical wall 12 and the outer vertical wall 14 near the ends 28, 30 of the inner vertical wall 12. As a result, the inner vertical wall 12 and the outer vertical wall 14 are free to flex towards each other near their ends. This enables the applicator device 10 to better conform to the mouth size of a user and therefore become more comfortable.

The horizontal shelf 16 extends from the inner vertical wall 12 to approximately halfway between the top edge 32 and the bottom edge 34 of the inner vertical wall 12. As a result, the inner vertical wall 12 extends both above and below the horizontal shelf 16. Likewise, the horizontal shelf 16 extends from the transition zone 44 of the outer vertical wall 14. As a result, the upper section 40 of the outer vertical wall 14 extends above the horizontal shelf 16 and the lower section 42 of the outer vertical wall 14 extends below the horizontal shelf 16.

The inner vertical wall 12, the horizontal shelf 16 and the upper section 40 of the outer vertical wall 14 create the upper lip chamber 18. The inner vertical wall 12, the horizontal shelf 16 and the lower section 42 of the outer vertical wall 14 create the larger lower lip chamber 20.

A volume of viscous medication 26, such as an anesthetic, is applied to the surfaces of both the upper lip chamber 18 and the lower lip chamber 20. The inner vertical wall 12 is then placed into the user's mouth, behind the lips 22, 24 and in front of the teeth 36. When in this position, the patient's upper lip 22 can be rested in the upper lip chamber 18. Likewise, the patient's lower lip 24 can be placed in the lower lip chamber 20. Once the upper and lower lips 22, 24 are in the upper and lower lip chambers 18, 20, the lips 22, 24 come into contact with the medication 26. The lips 22, 24 can be left in contact with the medication 26 for a prolonged period of time. This provides the medication 26 with enough time to fully effect the tissue of the lips 22, 24. If the medication 26 is a topical anesthetic, the lips 22, 24 are left in contact with the anesthetic until the lips 22, 24 are completely numb. Once the lips 22, 24 are numb, the application device 10 is removed and the physician is free to perform a medical procedure upon the lips 22, 24.

Figure 5:
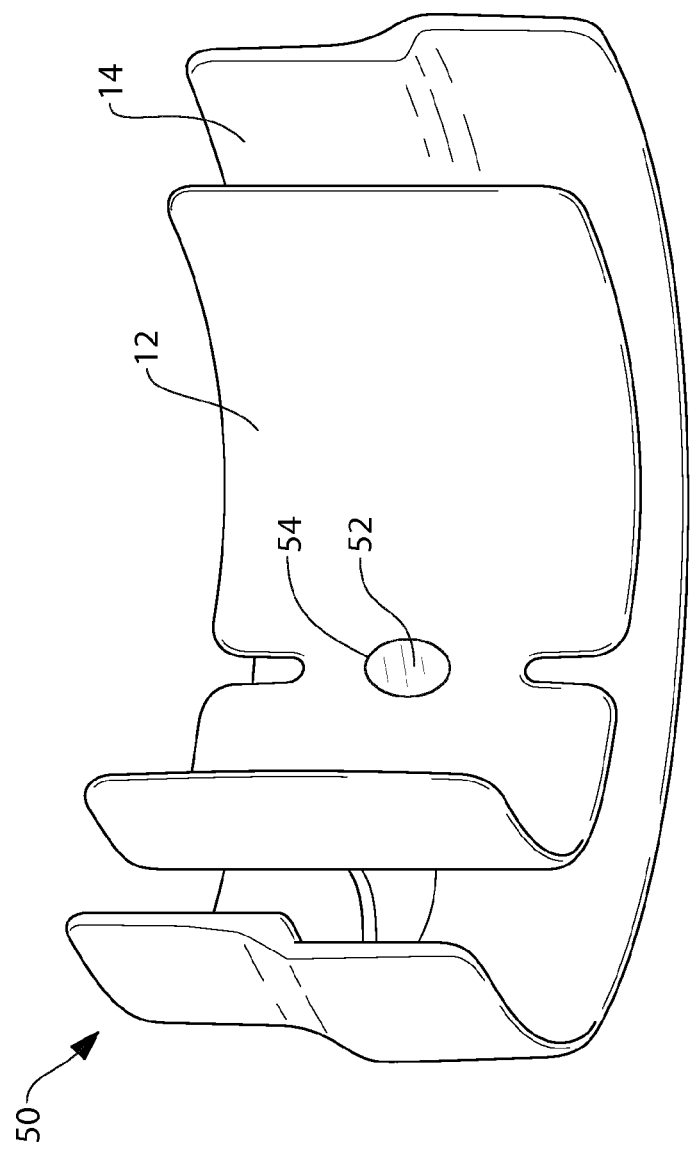
FIG. 5 is a rear perspective view of an alternate embodiment of the present invention applicator device.

Referring to FIG. 5, an alternate embodiment of the present invention applicator 50 is shown. This embodiment has the same configuration and parts as the embodiment of FIGS. 1-4. However, in this alternate embodiment, a conduit 52 is formed in the center of the applicator device 50. The conduit 52 has a first open end 54 that extends through the inner vertical wall 12 and an opposite second open end (not shown) that extends through the outer vertical wall 14. The presence of the conduit 52 enables a person to breathe better through their mouth while the applicator device 50 is being used.

It will be understood that the embodiments of the present invention that are illustrated and described are merely exemplary and that a person skilled in the art can make many variations to those embodiments. For instance, the dimensions of the inner vertical wall, outer vertical wall and horizontal shelf can all be varied to match different mouth sizes. All such embodiments are intended to be included within the scope of the present invention as defined by the claims.

What is claimed is:

1. For use with a person having a mouth with a lip and teeth, a method of topically applying material to a person's lips, comprising the steps of:
    providing an applicator device having a curved lip compartment defined between a first wall and a second wall, wherein said curved lip compartment defines a gap between said first wall and said second wall that is between 0.50 inches and 0.625 inches wide;
    placing said material within said curved lip compartment between said first wall and said second wall; and
    placing said second wall of said curved lip compartment within a person's mouth between the lip and teeth, wherein said lip passes into curved lip compartment and is brought into direct contact with said material therein.

2. The method according to claim 1, wherein said material is a topical anesthetic.

3. The method according to claim 1, wherein a horizontal shelf extends between said first wall and said second wall, wherein said first wall, said horizontal shelf and said second wall define three sides of said curved lip compartment.

4. The method according to claim 3, wherein said first wall and said second wall follow parallel paths, and said horizontal shelf lay perpendicular to both said first wall and said second wall.

5. The method according to claim 3, further including the step of providing at least one labial frenulum recess in said second wall.

6. For use with a person having a mouth with an upper lip, a lower lip, and teeth, a method of topically applying an anesthetic to said upper lip and said lower lip, comprising the steps of:
providing an applicator device having a curved first wall, a curved second wall, and a horizontal shelf that joins said first wall to said second wall, wherein said first wall, said second wall and said horizontal shelf combine to define an upper curved lip compartment and a lower curved lip compartment;
placing a volume of said anesthetic within said upper curved lip compartment and said lower curved lip compartment;
placing said second wall within a person's mouth and positioning said second wall between behind said upper lip and said lower lip in front of the teeth, wherein the upper lip passes into said upper curved lip compartment and the lower lip passes into said lower curved lip compartment, wherein the upper lip and the lower lip are contacted by said anesthetic.

7. The method according to claim 6, wherein said step of providing an applicator device includes providing an applicator device having a lower curved lip compartment that is larger than said upper curved lip compartment.

8. The method according to claim 6, wherein said first wall and said second wall follow parallel paths, and said horizontal shelf lay perpendicular to both said first wall and said second wall.

9. The method according to claim 6, further including the step of providing labial frenulum recesses in said second wall.

10. The method according to claim 6, wherein said upper curved lip compartment defines a gap between said first wall and said second wall that is at least 0.5 inches wide.

11. The method according to claim 10, wherein said lower curved lip compartment defines a gap between said first wall and said second wall that is no greater than 0.625 inches wide.

12. The method according to claim 6, wherein said first wall has two ends and said second wall has two ends, wherein said horizontal shell interconnects said first wall and said second wall in a center region midway between said first wall ends and said second wall ends.

13. The method according to claim 12, wherein open areas exist between said first wall and said second wall, proximate said first wall ends and said second wall ends where no horizontal shelf is present between said first wall and said second wall.

14. The method according to claim 6, further including the step of providing an open ended conduit that extends through said applicator device from said first wall to said second wall.

15. The method according to claim 6, wherein said second wall has a height of between one inch and two inches.

16. A method of topically applying an anesthetic to a lip of the mouth, said method comprising the steps of:
providing an applicator device that defines a curved lip compartment having an inner wall, an outer wall, a bottom shelf and an open top;
placing a volume of said anesthetic within said curved lip compartment; and
placing a user's lip into said curved lip compartment so that said inner wall is interposed between the user's lip and teeth, and where said lip is contacted by said anesthetic.

* * * * *